United States Patent [19]

Ishihara

[11] Patent Number: 5,344,844
[45] Date of Patent: Sep. 6, 1994

[54] SALT EXCRETION PROMOTING COMPOSITION

[75] Inventor: Kazuoki Ishihara, Sagamihara, Japan

[73] Assignee: Kabushiki Kaisya Advance, Japan

[21] Appl. No.: 999,552

[22] Filed: Dec. 30, 1992

Related U.S. Application Data

[63] Continuation of Ser. No. 688,559, Jun. 25, 1991, abandoned.

[30] Foreign Application Priority Data

Jan. 9, 1990 [JP] Japan ..................... 2-1003

[51] Int. Cl.$^5$ ............... A01N 37/12; A01N 43/04; A61K 9/14
[52] U.S. Cl. .................... 514/540; 514/903; 514/54; 514/960; 424/484
[58] Field of Search ............ 514/540, 54, 960, 970, 514/903; 424/484, 79; 435/26

[56] References Cited

U.S. PATENT DOCUMENTS

| | | | |
|---|---|---|---|
| 4,261,985 | 4/1981 | Biollaz | 514/177 |
| 4,470,975 | 9/1984 | Berger et al. | 514/869 |
| 4,676,976 | 6/1987 | Toba et al. | 424/484 |
| 4,808,353 | 2/1989 | Nambu et al. | 424/423 |
| 4,812,315 | 3/1989 | Tarabishi | 424/466 |
| 5,002,934 | 3/1991 | Norton et al. | 514/54 |
| 5,024,998 | 6/1991 | Bodor | 514/58 |

OTHER PUBLICATIONS

JP-A-59 143 559 (Gorou Imamichi) Aug. 17, 1984.
Nippon Kasei Gakkai shi, vol. 39 No. 3, pp. 187-195 (1988).

*Primary Examiner*—Michael G. Wityshyn
*Assistant Examiner*—Louise N. Leary
*Attorney, Agent, or Firm*—Finnegan, Henderson, Farabow, Garrett & Dunner

[57] ABSTRACT

A salt-excretion promoting composition, characterized by containing (i) 10 parts by weight of agar and (ii) 1 to 15 parts by weight of at least one polysaccharide selected from the group consisting of sodium alginate, λ- and κ-carrageenan and xanthane gum.

7 Claims, No Drawings

SALT EXCRETION PROMOTING COMPOSITION

This application is a continuation, of application Ser. No. 07/688,559, filed Jun 25, 1991, now abandoned.

TECHNICAL FIELD

The present invention relates to a novel sodium excretion-promoting composition. More particularly, the present invention relates to a composition which is useful in promoting the excretion of sodium ion contained in the cavity of the digestive tract by ingestion, which is in a dry state, is highly swellable in a salt solution such as a physiological saline, and is not digested in the digestive tract.

BACKGROUND ART

Currently, it is considered that many food fibers which are not digestive promote the excretion of sodium ion, and serve to excrete toxic substances. These functions of food fibers are primarily attributed to (1) the ion exchange capacity thereof, and (2) the swellability (water retention) thereof. Many food fibers have an ion exchange capacity of about 0.1–0.4 meq/g (Nihon-Kaseigakukai-Si 39, 187–195(1988)), and thus, for an adsorption of sodium corresponding to 1 g of sodium chloride, it is necessary to ingest 40–200 g (dry weight) of food fibers; it is difficult, however, in everyday life, to ingest such an amount of food fibers. Regarding the swellability (water retention) thereof, agar can absorb and retain an amount of about four times the dry weight of a solution, alginic acid can absorb and retain an amount of about four to five times the dry weight of the solution, and wheat bran can absorb and retain an amount of about four times the dry weight of the solution. One gram of such food fibers can retain about 4 g of humor (liquor in the cavity of the digestive tract), which contains an amount of sodium corresponding to about 30 mg of sodium chloride. Therefore, to excrete 1 g of sodium chloride, it is necessary to ingest 30 to 40 g of food fibers, and although such an ingestion is not impossible, it is difficult to continue for a long time.

DISCLOSURE OF THE INVENTION

Accordingly, the object of the present invention is to solve the problem of prior art as mentioned above and to provide a salt excretion-promoting composition having a high ion exchange capacity and swellability (water retention).

Other objects and features of the present invention will be apparent from the following description.

In accordance with the present invention, there is provided a salt excretion-promoting composition characterized by containing (i) 10 parts by weight of agar and (ii) 1 to 15 parts by weight of at least one polysaccharide selected from the group consisting of sodium alginate, λ- and κ-carrageenan and xanthane gum

BEST MODE OF CARRYING OUT OF THE INVENTION

To attain the above-mentioned object, the present inventors made an intensive study, and consequently, found that the dry substance obtained by dissolving a mixture of the agar and the polysaccharide such as sodium alginate, λ- or κ-carrageenan or xanthane gum, in hot water, and solidifying (or gelling) the solution by cooling, followed by air-drying at an ordinary temperature, has a remarkably high swellability in a salt solution of such a physiological saline, and thus completed the present invention.

The ratio of agar to the other polysaccharide(s) in the mixture is preferably 1:0.1 to 1:1.5 (by weight), more preferably 1:0.5 to 1:1.0.

EXAMPLES

The invention is illustrated by the following examples, and it is understood that the scope of the invention is not limited to these examples.

An amount of 1% of agar and various amounts (% by weight based on the weight of the aqueous solution) of sodium alginate, λ-carrageenan and κ-carrageenan were dissolved in hot water, and the solution was cooled and set (gelatinized). The obtained solid was then slowly air-dried at an ordinary temperature, and the swellability (the rate of the weight after swelling to the weight before swelling, in a physiological saline) of the thus-obtained dry substance was as shown in Table 1.

TABLE 1

| Additive other than agar (% by weight) | | Swellability |
| --- | --- | --- |
| Sodium alginate | 1.0 | 32 |
| Sodium alginate | 0.5 | 25 |
| Sodium alginate | 0.2 | 18 |
| Sodium alginate | 0.1 | 12 |
| Gum arabic | 1 | 8.7 |
| λ-Carrageenan | 1 | 32 |
| κ-Carrageenan | 1 | 29 |
| Xanthane gum | 0.1 | 10 |
| Xanthane gum | 0.5 | 20 |
| Sodium alginate | 1.0 | |
| (Drying by heating at 60° C.) | | 13 |
| (Drying by heating at 80° C.) | | 7.5 |

The swellability was determined by leaving the dry substance to stand in a physiological saline (at 37° C., for 2 hours), taking out the formed gel, removing any solution adhering to the gel, measuring the total weight, and then dividing the total weight by the weight of the original dry substance.

UTILIZABILITY IN INDUSTRY

As described above, according to the present invention, a remarkably swellable composition can be obtained, 3.3 to 4 g of the composition being satisfactory for the excretion of 1 g of sodium chloride, and the composition can be easily ingested in combination with other foods. Furthermore, the composition of the present invention can be used in the form of a powder, granule or the like, in combination with a salt solution such as physiological saline, or can be used in the form of the composition dispersed in a salt solution such as a physiological saline.

I claim:

1. A method for promoting the excretion of sodium ion contained in the cavity of the digestive tract of a human, which comprises administering to a human a dietary composition comprising (i) 10 parts by weight of agar and (ii) 1 to 15 parts by weight of at least one polysaccharide selected from the group consisting of sodium alginate, λ-and κ-carrageenan and xanthane gum in an amount effective to promote said excretion of sodium ion.

2. A method as claimed in claim 1, wherein said comprising agar and polysaccharide is obtained by dissolving a mixture thereof in water, gelatinizing the solution, and then air-drying the gel.

3. A method as claimed in claim 1, wherein said composition is in a powder or granule form.

4. A method as claimed in claim 3, wherein the composition is used in combination with a salt solution.

5. A method as claimed in claim 4, wherein said salt solution is a physiological saline.

6. A method as claimed in claim 1, wherein said effective amount is from about 3—3 to about 4 grams of said composition per 1 gram of sodium ion to be excreted.

7. A method as claimed in claim 1, wherein said composition is ingested by said human.

* * * * *

UNITED STATES PATENT AND TRADEMARK OFFICE
CERTIFICATE OF CORRECTION

PATENT NO. : 5,344,844
DATED : September 6, 1994
INVENTOR(S) : Kazuoki Ishihara

It is certified that error appears in the above-indentified patent and that said Letters Patent is hereby corrected as shown below:

Column 2, line 60, change "$\lambda$-and" to --$\lambda$- and--.

Claim 2

Column 2, line 63, after "said" insert --composition--.

Claim 6

Column 4, line 1, change "3-3" to --3.3--.

Signed and Sealed this

Eighth Day of November, 1994

Attest:

BRUCE LEHMAN

Attesting Officer    Commissioner of Patents and Trademarks